United States Patent [19]

Smalley et al.

[11] Patent Number: Plant 6,227

[45] Date of Patent: Jul. 19, 1988

[54] ELM TREE NAMED INDEPENDENCE

[75] Inventors: Eugene B. Smalley, Cottage Grove, Wis.; Donald T. Lester, Portland, Oreg.

[73] Assignee: Elm Research Institute, Harrisville, N.H.

[21] Appl. No.: 787,672

[22] Filed: Oct. 15, 1985

[51] Int. Cl.[4] ..... A01H 5/00
[52] U.S. Cl. ..... Plt./51
[58] Field of Search ..... Plt./51

[56] References Cited

U.S. PATENT DOCUMENTS

P.P. 3,108 4/1972 Flemer et al. ..... Plt. 51
P.P. 3,780 9/1975 Smalley et al. ..... Plt. 51
P.P. 5,335 11/1984 Smalley et al. ..... Plt. 51

*Primary Examiner*—James R. Feyrer
*Attorney, Agent, or Firm*—Klarquist, Sparkman, Campbell, Leigh & Whinston

[57] ABSTRACT

An elm tree characterized by high resistance to Dutch Elm Disease.

1 Drawing Sheet

The present invention relates to a new and distinct variety of an American elm (*Ulmus americana*) named Independence. The variety Independence is characterized by a high degree of resistance to Dutch Elm Disease caused by *Ceratocystis ulmi*, and reduced susceptibility to *Stegophora ulmea* (black leaf spot disease,) *Verticillium dahliae* (Verticillium wilt,) and *Taphrina ulmi* (leaf blister disease.)

The cultivar Independence is derived from a cross between the widely grown cultivar "Moline" and pollen from a male tree initially grown at Interstate Nurseries of Hamburg, Iowa. It is one of a number of clones known as 'American Liberty' elms demonstrating resistance to disease, particularly Dutch Elm Disease, and possessing a desirable upright vase-shape and vigorous growth habit. Ramets of the female parent of Independence survive at Arlington, Wis. and other locations. The current status of the female parent is not known. The male parent, designated W185-21, was the result of disease resistance screening initiated at Arlington, Wis. in 1960. The W185-21 tree died in 1973 after inoculation with a particularly virulent mixture of *C. ulmi* from North American sources.

General characteristics of the variety Independence include an upright vase shape, dense foliation, and vigorous growth rate. It develops a substantially upright main trunk during early growth stages with older branches becoming primarily horizontal at maturity. It propagates easily and establishes well in field testing.

The accompanying drawing shows a spcimen tree of the new variety in early fall coloration illustrating its general form and habit of growth.

General leaf size, shape, color, bark color/texture, and other growth characteristics are not distinctive and typical of North American white elms. The technical and descriptive information regarding leaves, bark, and other growth characteristics of the variety Independence tree are provided herein in compliance with statutory disclosure requirements, and are not distinguishing features of the tree. The mature leaves exposed to full sun are a dark "parsley green" (00962) (Wilson, R. 1941. Horticultural Colour Chart. Vol. 2. British Colour Council, London.) on their upper sides, and are glabrous or slightly pubescent with scattered trichomes bent parallel to the surface and pointing toward the tip. The lower surfaces of the leaves are "spinach green" (0960/3) (Wilson, supra) ranging from downy-pubescent to glabrous. Pubescence tends to be a juvenile characteristic found mainly on the most vigorous shoots of the tree, while leaves on less vigorous branches are always glabrous. All phases of pubescence can be found on a single tree.

Mature leaves are ovate-elliptical, unequal at the base, sharply acuminate at the tip, and doubly serrate at the margins. Many of the sprout leaves develop a vestigial petiolar leaflet. Often these leaflets are fairly large, resulting in near compound-leaf form.

Fall leaf color characteristics are variable. However, the leaves frequently turn a bright golden yellow with abscission occurring in late September or early October (in south central Wisconsin.)

Specific leaf characteristics as derived from greenhouse tests are described as follows in Table 1.

TABLE 1

| |
|---|
| Average leaf length = 15.0 to 16.5 cm |
| Average leaf width = 8.5 to 11.5 cm |
| Average petiole length = 0.8 to 0.9 cm |
| Average growth rate = 0.85 cm/day* |

*(Growth rate was measued during log phase on greenhouse grown plants in five inch pots from dormancy broken one-year-old rooted cuttings bud pruned at bud break to allow the growth of a single dominant shoot. The comparison was carried out at temperatures of 24° C. day - 18° C. night under a 16 hour day supplied by supplemental illumination.)

Newly formed bark develops in varying shades of brown, but after aging, changes to a gray color. With maturity, cracks having broad, flat, and scaly ridges are formed in the bark.

ASEXUAL REPRODUCTION

Propagation can be carried out in a greenhouse using root cuttings allowed to sprout in moist sphagnum peat and sand. Propagation originally took place at the University of Wisconsin in Madison, Wis. under the direction of the Department of Plant Pathology. Greenhouse temperatures are adjusted to 180° C. at night, and 24° C. during the day, with 16 hour days supplied by supplemental illumination. Greenwood cuttings dipped in rooting hormone can be transplanted as rooted cuttings after approximately 20 days in a perlite-peat rooting medium under fine intermittent mist.

DETERMINATION OF RESISTANCE TO DUTCH ELM DISEASE

Methods for screening elm introductions and breeding progeny for Dutch Elm Disease resistance have been previously described (Lester, D. T., and E. B. Smalley, 1972. Improvement of Elms Through Interspecific Hybridization With Asian Species. IUFRO Genetics-Sabrao Joint Symposia, Tokyo 1972. C-5 (V):1-10; Smalley, E. B., and A. G. Kais, 1966. Seasonal Variations in the Resistance of Various Elm Species to Dutch Elm Disease, in H. D. Gerbold et al., (eds.) *Breeding Pest Resistance Trees,* Pergamon Press, NY, pp. 279-292.)

In the case of the variety Independence and other so-called 500 series American Liberty elm trees, control-pollinated seedlings were grown for one year in outdoor seedbeds and transplantd to field locations in the second year. Thereafter, the seedlings were inoculated with *C. ulmi* the following spring. The inoculum consisted of a mixture of isolates from Wisconsin, Kansas, Massachusetts, Illinois, Nebraska, Minnesota, Connecticut, and Maine. Selected survivors which developed less than 10% crown damage were then increased vegetatively in 1975 and grown in replicated field plantings for another two years. In 1978, selected ramets of each 500 series elm were inoculated with the *C. ulmi* mixture at differing periods during the growing season. Observations on disease development were recorded periodically for the following year. The results of these tests on the Independence, therein identified as clone W-510, are set forth in Table 2, together with results of tests on other clones. At the top of the table, the dates of inoculation are listed. At "T", the number of ramets without symptoms after inoculation versus the total number of ramets inoculated with *C. ulmi* is shown. Beneath these numbers is a calculation of the percentage of ramets that did not show symptoms of Dutch Elm Disease after inoculation.

TABLE 2

| Clone | | Ramets without symptoms[y] Dates of inoculation[x] | | | | |
|---|---|---|---|---|---|---|
| | | 5/25 | 6/1 | 6/7 | 6/14 | 6/21 |
| | | | Unselected[u] | | | |
| W-411-3 | T | 3/7 | 0/8 | 0/6 | 0/4 | 1/12 |
| | % | 42.9 | 0 | 0 | 0 | 8.3 |
| W-412-1 | T | 1/12 | 1/9 | 2/11 | 0/5 | 0/12 |
| | % | 8.3 | 11.1 | 18.2 | 0 | 0 |
| | | 'American Liberty'- 500 series[w] | | | | |
| W-502 | T | — | 0/2 | — | — | — |
| | % | — | 0 | — | — | — |
| W-503 | T | 0/6 | 0/6 | 0/4 | 1/5 | 2/6 |
| | % | 0 | 0 | 0 | 20 | 33.3 |
| W-505 | T | — | — | — | — | — |
| | % | — | — | — | — | — |
| W-507 | T | 5/6 | — | — | 0/1 | 1/2 |
| | % | 83.3 | — | — | 0 | 50 |
| W-510 | T | 2/11 | 3/4 | 0/12 | 2/8 | 2/5 |
| | % | 18.2 | 75 | 0 | 25 | 40 |
| | | 'American Liberty'- "Topeka" Cultivar[v] | | | | |

TABLE 2-continued

| Clone | | Ramets without symptons[y] Dates of inoculation[x] | | | | |
|---|---|---|---|---|---|---|
| | | 6/28 | 7/6 | 7/18 | 8/3 | All Dates[z] |
| | | | Unselected[u] | | | |
| W-411-3 | T | — | 0/6 | 0/9 | 3/3 | 7/55 |
| | % | — | 0 | 0 | 100 | 12.73 |
| W-412-1 | T | — | 0/10 | 1/9 | 2/2 | 7/70 |
| | % | — | 0 | 11.1 | 100 | 10.00 |
| | | 'American Liberty'- 500 series[w] | | | | |
| W-502 | T | — | 4/6 | 4/6 | — | 8/14 |
| | % | — | 66.7 | 66.7 | — | 57.14 |
| W-503 | T | 0/2 | 1/5 | 3/3 | 2/2 | 9/39 |
| | % | 0 | 20 | 100 | 100 | 23.1 |
| W-505 | T | — | 5/5 | 1/1 | — | — |
| | % | — | 100 | 100 | — | — |
| W-507 | T | 2/2 | 3/5 | 2/2 | — | 13/18 |
| | % | 100 | 60 | 100 | — | 72.2 |
| W-510 | T | 6/9 | 4/9 | 7/8 | 1/1 | 27/67 |
| | % | 66.7 | 44.4 | 87.5 | 100 | 43.3 |
| | | 'American Liberty'- "Topeka" Cultivar[v] | | | | |
| M-8 | T | 8/8 | 5/5 | 7/8 | 2/2 | 35/56 |
| | % | 100 | 100 | 87.5 | 100 | 62.5 |
| M-8 | T | 1/5 | 1/8 | 3/5 | 2/7 | 6/8 |
| | % | 20 | 12.5 | 60 | 28.6 | 75 |

[x]Mixed inoculum from isolates of *Ceratocystis ulmi* from Wisconsin, Kansas, Massachusetts, Illinois, Nebraska, Minnesota, Connecticut and Maine.
[y]Trees planted as rooted cuttings, 3 plants per clone per block, 15 clones per block, and 36 to 40 blocks per series. (Many clones are incompletely represented in blocks because of transplant mortality or shortage of plants.) Data is derived from 1971-72, 1974-75 and 1978-79 series and not all clones in the studies are shown.
[z]Underlined data indicates the approximate period of highest susceptibility.
[u]Data from 1971-72
[v]Data from 1973-74
[w]Data from 1978-79

As indicated in Table 2, the Independence elm presents high resistance to Dutch Elm Disease as compared with other varieties. It is not as resistant as some varieties, but its susceptible period (early June) is shorter than that of other tested varieties. The physiological basis for resistance to *C. ulmi* is not presently understood. Preliminary research suggests an ability of the tree to illicit antifungal phytoalexins in response to the presence of *C. ulmi* spores. Research as described in Smalley, E. B., N. S. Ehlke, E. E. Clark, and S. H. Mai. 1982. Condial reactions in Ulmus following inoculation with *Ceratocystis ulmi. Phytopathology* 72:981 suggests that such capability increases with plant age, both seasonally and with developing maturity.

Field observations also suggest that the Independence elm is not unduly susceptible to black leaf spot disease caused by *Stegophora ulmea* (Schw: Sydow and Sydow). It also exhibits tolerance to *Verticillium dahliae Kleb* (the casual agent of Verticillium wilt) and *Taphrina ulmi* (leaf blister diseases.) Furthermore, because the growth characteristics of the tree involve an upright growth habit and acute branching angle, it has demonstrated resistance to severe winds and ice storms.

I claim:

1. A new and distinct variety of elm tree as shown and described herein primarily characterized by a short period of susceptibility to Dutch Elm Disease, vigorous growth rate, and ease of propagation.

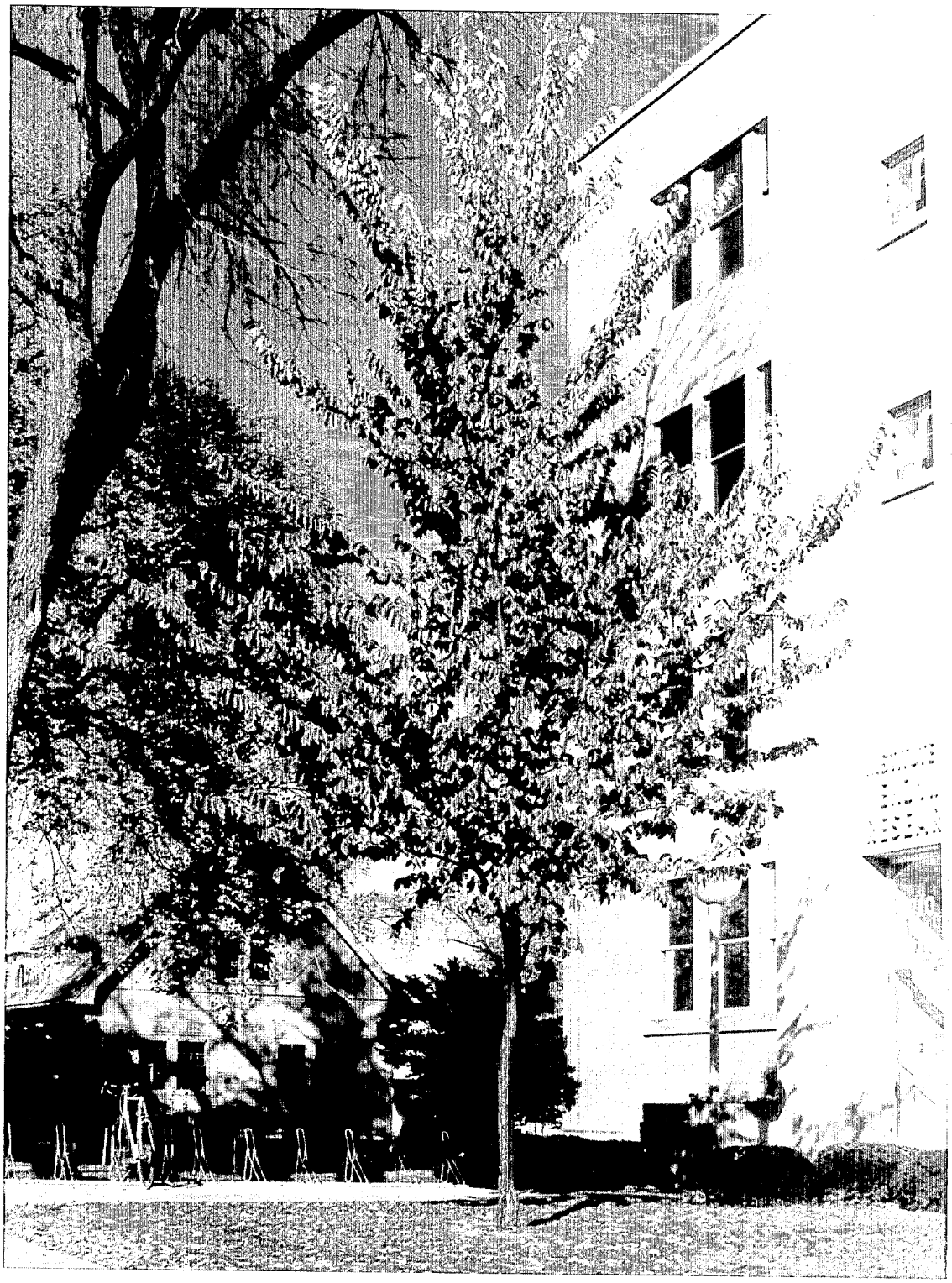

* * * * *